(12) United States Patent
Ogle et al.

(10) Patent No.: US 6,491,617 B1
(45) Date of Patent: Dec. 10, 2002

(54) MEDICAL DEVICES THAT RESIST RESTENOSIS

(75) Inventors: Matthew F. Ogle, St. Paul, MN (US); Peter S. Dardi, St. Paul, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/476,745

(22) Filed: Dec. 30, 1999

(51) Int. Cl.[7] .................................................. A61N 5/00
(52) U.S. Cl. .......................................................... 600/3
(58) Field of Search ............................... 600/1–8; 623/1, 623/11, 12; 604/53, 265; 435/7.1; 424/1.49, 423

(56) References Cited

U.S. PATENT DOCUMENTS

| | | | |
|---|---|---|---|
| 5,102,402 A | 4/1992 | Dror et al. | 604/265 |
| 5,632,981 A | 5/1997 | Saavedra et al. | 424/78.08 |
| 6,013,106 A | 1/2000 | Tweden et al. | |
| 6,096,070 A | * 8/2000 | Ragheb et al. | 623/1 |
| 6,106,454 A | * 8/2000 | Berg et al. | 600/3 |
| 6,179,789 B1 | * 1/2001 | Tu et al. | 600/585 |
| 6,238,872 B1 | * 5/2001 | Mosseri | 435/7.1 |

FOREIGN PATENT DOCUMENTS

| | | |
|---|---|---|
| EP | 0 819 446 A2 | 1/1998 |
| EP | 0 832 618 A1 | 4/1998 |
| WO | WO 97/09006 | 3/1997 |
| WO | WO 97/27886 | 8/1997 |
| WO | WO 98/31404 | 7/1998 |

* cited by examiner

*Primary Examiner*—Kevin Shaver
*Assistant Examiner*—Brian Szmal
(74) *Attorney, Agent, or Firm*—Patterson, Thuente, Skaar & Christensen, P.A.; Peter S. Dardi; Hallie A. Finucane

(57) ABSTRACT

Medical devices include biocomatible materials and a plurality of exogenous storage structures. The exogenous storage structures store a therapeutic agent which acts to inhibit restenosis. In some embodiments, the therapeutic agents are radioactive metal ions. In other embodiments, the medical device has an expandable structure with particles of therapeutic agent on its surface. The particles of therapeutic agent are delivered into a region susceptible to restenosis by direct application of the medical device against the adjacent wall.

31 Claims, 2 Drawing Sheets

MEDICAL DEVICES THAT RESIST RESTENOSIS

BACKGROUND OF THE INVENTION

The invention relates to medical devices associated with agents that inhibit restenosis.

Prostheses, i.e., prosthetic devices, are used to repair or replace damaged or diseased organs, tissues and other structures in humans and animals. Prostheses must be generally biocompatible since they are typically implanted for extended periods of time. Prostheses can be constructed from natural materials such as tissue, synthetic materials or a combination thereof.

Invasive procedures are commonly used to treat various forms of cardiovascular disease. Routine procedures include angioplasty, atherectomy, insertion of stents and laser surgery. However, damage resulting from this contact with a patient's blood vessels can result in restenosis, the blockage of blood vessels. In particular, balloon angioplasty and atherectomy are associated with relatively high incidents of restenosis in the three to six months following the procedure.

A common procedure for treating arteriosclerosis is balloon angioplasty. To perform balloon angioplasty, a catheter is guided through an artery to a location with restricted flow. A balloon catheter is then inflated to a pressure between, for example, 3 and 6 atmospheres for about 60 seconds. The inflation of the balloon cracks the plaque lining the vessel walls stretching the arterial wall, so that the lumen of the artery is expanded following the inflation of the balloon. The increased lumen allows for increased blood flow, but restenosis can result in subsequent loss of blood flow through the lumen.

Vascular stents involve structures that are expanded within a blood vessel to maintain or expand the lumen of the vessel. While intravascular stents can be used to successfully achieve increased internal lumen diameter, stent restenosis also can result in intimal thickening that reduces the effectiveness of the stent.

Restenosis is characterized by platelet aggregation and adhesion, and by smooth muscle cell migration and proliferation, which individually or together result in the narrowing of the vessel lumen. The narrowing of the vessel restricts vasodilation and causes an increase in blood pressure. The smooth muscle cells along the vessel lining being proliferating within two to three days of disruption of the vessel and continue for several days. In addition to vessel narrowing, restenosis can lead to blood clotting, which further threatens stroke, lung damage and heart damage if the blood clots travels from the formation site. Some approaches for the prevention or treatment of restenosis include the delivery of radioactive compounds or of nitric oxide, which is implicated in platelet accumulation.

SUMMARY OF THE INVENTION

In a first aspect, the invention pertains to a medical device suitable for implantation including a biocompatible material and a plurality of exogenous biological macromolecules bound to the biocompatible material. The exogenous biological macromolecules store a therapeutic agent which acts to inhibit restenosis.

In another aspect, the invention pertains to a medical device suitable for implantation comprising a biocompatible material and a plurality of exogenous storage structures bound to the biocompatible material. The exogenous storage structures store isotopically enhanced radioactive metal ions.

In a further aspect, the invention pertains to a method for inhibiting restenosis comprising binding an exogenous storage structure to a biocompatible material forming at least a portion of a vascular prosthesis. The storage structure comprises a biological macromolecule. The method further includes associating the storage structure with a therapeutic agent which acts to inhibit restenosis.

In addition, the invention pertains to a medical device suitable for implantation comprising a biocompatible material and a therapeutic agent covalently bonded to the biocompatible material. The therapeutic agent actsa to inhibit restenosis.

In another aspect, the invention pertains to a medical device including an expandable structure and therapeutic particles on the surface of the expandable structure. The therapeutic particles include a therapeutic agent that acts to inhibit restenosis.

Furthermore, the invention pertains to a method of producing a medical device comprising applying therapeutic particles to the exterior of an expandable structure. The therapeutic particles include a therapeutic agent that inhibits restenosis.

DETAILED DESCRIPTION OF THE ILLUSTRATIVE EMBODIMENTS

Figure 1:
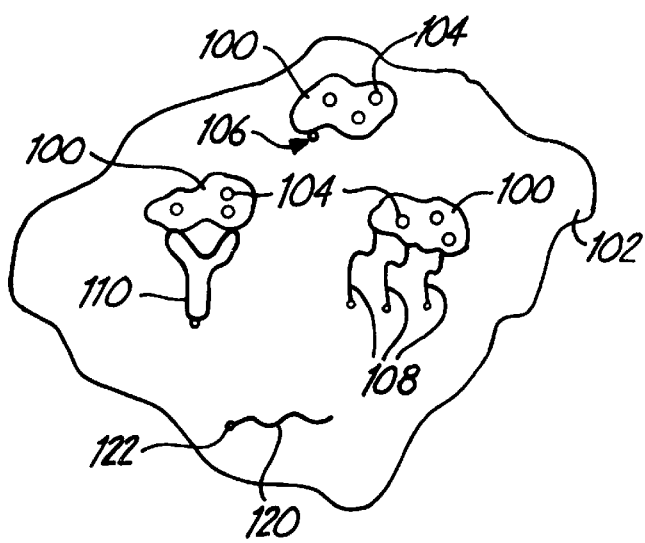
FIG. 1 is a schematic diagram that shows a medical device having bound exogenous storage structures associated with a therapeutic agent.

Therapeutic agents can be delivered locally to vascular sites that have been subjected to intervention, where the agent is effective to inhibit restenosis, i.e., to reduce the severity and/or to reduce or eliminate the incidence of restenosis. The intervention sites generally are subject to some form of treatment for vascular disease. "Vascular" sites and structures as used herein include cardiovascular sites and structures and other blood contacting sites and structures. Furthermore, the treatment of strictures of the urinary tract are contemplated. Due to the medical treatment, these locations are prone to the development of restenosis. The therapeutic agents can be lethal or inhibitory to proliferating cells and/or inhibitory to deposition of platelets or other clotting agents.

Local delivery of the therapeutic agent can be directed to the specific potential restenosis sites without introducing larger systemic quantities of the therapeutic agent. In some embodiments, the local delivery of the agent involves the use of storage structures that carry and store the therapeutic agent in association with a medical device. The storage structures can be associated with a substrate that forms part of a medical device. In some alternative embodiments, a therapeutic agent is directly covalently bonded to the biocompatible material without the use of a binder matrix of an adhesive.

In alternative embodiments, the therapeutic agents are delivered as particulates that are delivered with the use of an expandable medical device. The expansion of the device delivers the therapeutic agent. In particular, an angioplasty balloon can be used to deliver therapeutic particles by inflating the balloon to open up the lumen of the blood vessel. The particulates are located initially on the surface of the balloon and are driven into the plaque and/or tissue of the vessel wall when the balloon in deployed. In some embodiments, the therapeutic agent is bound to extracellular matrix of the vessel with ultraviolet light.

A variety of medical articles can be used to contact bodily fluids or a patient. Relevant biocompatible medical articles generally incorporate a biocompatible material which is intended to contact the patient's biological fluids and/or tissues. Bodily fluids include, for example, blood, plasma, serum, interstitial fluids, saliva and urine. The patient can be an animal, especially a mammal, and preferably is a human.

Relevant medical articles include devices that contact a person's bodily fluids for varying lengths of time, for example, prostheses, catheters and surgical instruments. Prostheses, i.e., prosthetic articles, are used to repair or replace damaged or diseased organs, tissues and other structures in humans and animals. Prostheses generally must be biocompatible since they are typically implanted for extended periods of time. Preferred prostheses include prostheses used in the vascular system at locations prone to restenosis.

The therapeutic agents generally can be any agent effective for the inhibition of restenosis including agents that are toxic or inhibitory to proliferating smooth muscle cells or that inhibit platelet accumulation or adhesion. Preferred therapeutic agents include radioactive isotopes that emit radiation at a suitable rate to inhibit proliferating cells. Suitable radioactive ions include anions, such as $^{32}PO_4^-$, $^{125}I^-$, $^{131}I^-$, a cations of metals, such as, $^{69}Fe$, $^{67}Ga$, $^{59}Co$, $^{67}Cu$, $^{90}Y$, $^{99}Rh$, and $^{196}Au$. Nitric oxide is known to inhibit platelet aggregation, as described in U.S. Pat. No. 5,665,077 to Rosen et al., incorporated herein by reference. Preferred approaches for delivering nitric oxide generally involve the delivery of compounds that release nitric oxide.

Exogenous storage structures are macromolecular structures that are not inherent or native to the biocompatible material. In other words, the exogenous storage structures are joined to the biocompatible material to provide relevant storage capability to the biocompatible material or to enhance any low level inherent storage capability of the biocompatible material with respect to the therapeutic agent. Through the use of exogenous storage structures, a therapeutic agent can be delivered locally at a region, such as a blood vessel, susceptible to restenosis. For example, the therapeutic agent can be associated with the particular medical device whose use is correlated with the restenosis risk. Thus, an effective amount of therapeutic agent can be delivered locally without causing undesirable systemic treatment and possible toxicity. With local delivery of the therapeutic agent at the treatment site, only a small amount of therapeutic agent is required to yield an effective treatment.

Exogenous storage structures can provide flexibility in directing and maintaining the therapeutic agent at specific, particularly relevant portions of a medical article. Further, use of an exogenous storage structure permits control of the release rate of the therapeutic agent, if release is desirable for effectiveness of the therapeutic agent. The association of a therapeutic agent with the exogenous storage structures can be performed before or after attachment of the exogenous storage structures to the biocompatible material.

Generally, the exogenous storage structure is bound to biocompatible material forming the medical device or a portion thereof. This binding is shown schematically in FIG. 1. In the schematic diagram of FIG. 1, exogenous storage structures 100 are bound to biocompatible material 102. Exogenous storage structures 100 are associated with therapeutic agents 104.

FIG. 1 displays three possible storage structure binding approaches. For example, exogenous storage structures 100 can be bound to the biocompatible material 102 with a covalent bond 106. Alternatively, linkers 108 having a plurality of functional groups, such as crosslinking agents, can be used that form covalent bonds with both biocompatible material 102 and exogenous storage structures 100. Alternatively, a linker 110, such as an antibody, can bind with specific bonding interactions with exogenous storage structures 100 and/or biocompatible material 102.

In alternative embodiments, the therapeutic agent 120 is covalently bonded to biocompatible material 102, as shown in FIG. 1. A linker compound can be used in the formation of covalent bond 122. Any linker compound can be considered to be a portion of the therapeutic compound.

In alternative embodiments, the therapeutic agent is delivered from the surface of a medical device, such as an angioplasty balloon. The medical device generally expands, flexes or otherwise moves to apply some force against a blood vessel wall or other region susceptible to restenosis, e.g. a passageway of the urinary tract. The force of the angioplasty balloon or other device against the vessel wall or other region after the balloon or device is deployed propels the therapeutic agent into the plaque and/or tissue in the target region. The therapeutic agent can then be effective in inhibiting restenosis in the treated structure. The medical device used to deliver the therapeutic agent can be removed from the treated region or it can remain in the treated region.

The approaches described herein for delivery of therapeutic agents for the treatment of restenosis are an effective and versatile approach for treatment of restenosis. For example, local delivery of the therapeutic agent results in fewer side effects than systemic delivery, and a reduced amount of therapeutic agent is needed as compared to systemic delivery. The delivery approaches described herein provide effective control of the amount of therapeutic agent delivered at a location susceptible to restenosis. A variety of different therapeutic agents can be delivered alone or in combination.

Medical Articles

Relevant medical articles include a biocompatible material, at least as component, that is suitable for contacting a patient's bodily fluids and/or tissues. Biocompatible materials are non-toxic, non-carcinogenic and do not induce hemolysis or a severe immunological response. For embodiments based on exogenous storage structures, the medical articles generally are designed for implantation into a patient for extended periods of time. For embodiments based on the delivery of particulate therapeutic agents, the medical article can be designed for implantation, or the medical article can be used percutaneously extending from outside the body into the body for delivery of the therapeutic agent.

Suitable medical articles or components of such medical articles for implantation include, for example, artificial organs such as artificial hearts, anatomical reconstruction prostheses, coronary stents, vascular grafts and conduits, vascular and structural stents, vascular shunts, biological conduits, stents, valved grafts, permanently in-dwelling percutaneous devices, intrauterine devices (IUDs), urinary stents, and combinations thereof.

Other biomedical devices that are designed to dwell for extended periods of time within a patient are also suitable for the inclusion of therapeutic agents described herein. These devices include, for example, Hickman catheters and other percutaneous articles that are designed for use over a plurality of days. Percutaneous devices include items that penetrate the skin, thereby extending from outside the body into the body.

Medical devices of particular interest are susceptible to initiation of undesirable cell growth and/or platelet aggregation. Implantable devices of particular interest include, for example, implantable vascular devices, implantable cardiovascular devices and implantable urinary stents. Implantable vascular devices include, for example, vascular stents, vascular grafts and conduits and valved grafts. Implantable cardiovascular devices of particular interest include, for example, coronary stents.

Especially relevant medical articles for use with exogenous storage structures include, for example, vascular stents, urinary stents and vascular grafts, especially small vascular grafts. Vascular stents are used to form an internal scaffolding within the blood vessel that maintains or increases the lumen of the blood vessel. The stent is generally introduced through a catheter for deployment at the desired position within the blood vessel.

Figure 2:
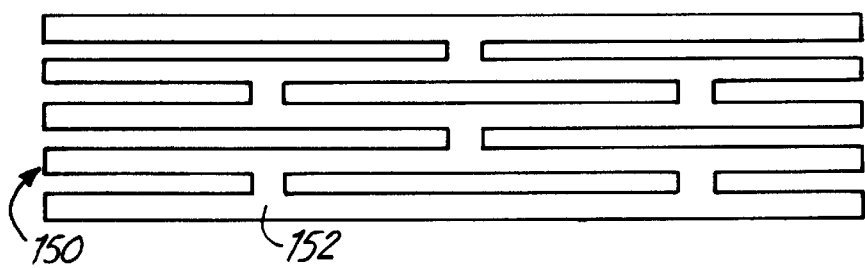
FIG. 2 is a side view of a vascular stent.
Figure 3:
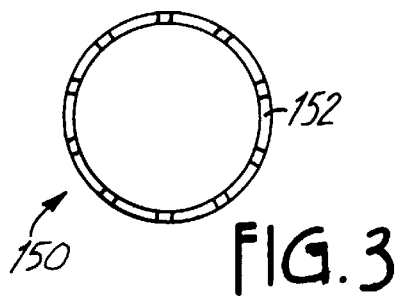
FIG. 3 is an end view of the vascular stent of FIG. 2.

Vascular stents generally are formed from synthetic materials, such as metals or synthetic polymers. The stent can be formed from a resorbable material, for example a resorbable polymer, such that the stent forms a temporary scaffolding to promote healing while maintaining patency of the blood vessel. A representative stent design is shown in FIGS. 2 and 3. Vascular stent 150 is formed from a biocompatible material 152 with a form consistent with its expandable nature.

Preferred vascular and urinary stents have radial and torsional flexibility, biocompatibility, visibility by x-ray, and reliable expandability. Expandability is desirable since vascular stents generally are implanted through a catheter. Thus, the vascular stent preferably expands to fit securely against the vessel walls once deployed. Expandable stents can operate, for example, with a spring-like design that expands from a small diameter to a predetermined dimension when a constraint is removed, or with a thermal memory metal that changes shape upon heating. In addition, a balloon expandable stent can undergo plastic deformation, expanding the material beyond its elastic limit with pressure. The biocompatible materials for forming these stents are described further below.

Vascular grafts are used to replace portions of damaged/diseased vascular tissue. The damaged/diseased section of vascular tissue is removed, and the vascular graft replaces the removed section. The vascular graft is attached with suture or other fasteners to the free ends of the vessel that remain after a damaged/diseased portion of vessel is extracted. The vascular graft can be constructed from tissue and/or synthetic materials, as described further below.

Figure 4:
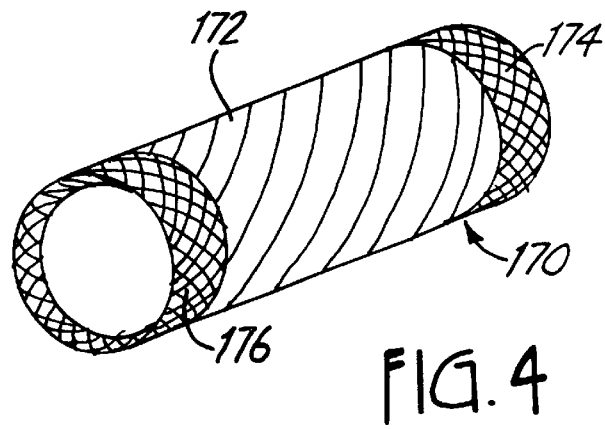
FIG. 4 is a perspective view of a vascular graft.
Figure 5:
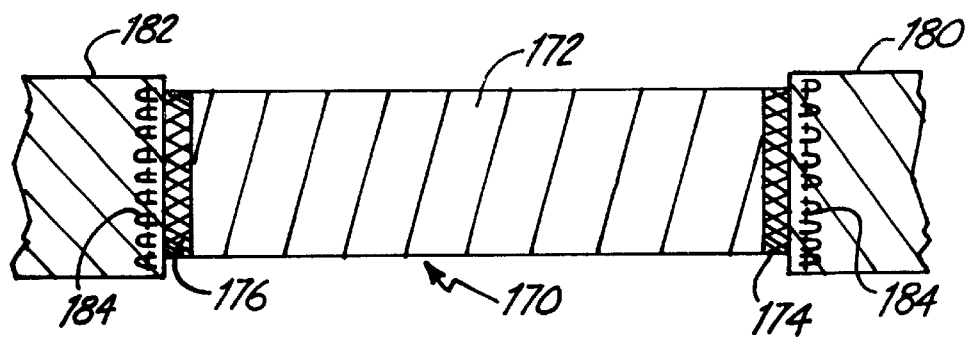
FIG. 5 is a side view of the vascular graft of FIG. 4 attached to a blood vessel.

A representative vascular graft 170 is depicted in FIG. 4. Vascular graft 170 includes a flexible tubular structure 172 and optional sewing cuffs 174, 176. Flexible tubular structure 172 can include one or more biocompatible materials, such as tissue, synthetic polymer or combinations thereof. Sewing cuffs 174, 176 are formed from fabric, tissue or the like. Sewing cuffs 174, 176 assist with the implantation of the prosthesis and may provide reinforcement of the prosthesis at the site of anastomoses, i.e., attachment of the vessel to the graft. A cross section of vascular graft 170 attached to natural vessel sections 180, 182 is depicted in FIG. 5. As shown in FIG. 5, suture 184 is used to secure vascular graft 170 to vessel sections 180, 182.

Restenosis is particularly problematic in thinner arteries. Embodiments of the vascular grafts and vascular stents of particular interest have an implanted internal diameter less than about 5 mm, less than about 4 mm or even less than about 3 mm.

In alternative embodiments involving the delivery of particulate therapeutic agents, particularly relevant medical devices for the delivery of the agent include expandable stents, angioplasty balloons, and surgical instruments. Angioplasty balloons are brought into a partially obstructed artery using a catheter. When positioned at the point of obstruction, the balloon is expanded under pressures generally in the range of 3–6 atmospheres. Similarly, a vascular stent is positioned within a vessel using a catheter and expanded against the vessel walls to increase the lumen. The force of the expanding balloon or stent can propel the particle of therapeutic agent into the tissue and/or plaque. Surgical instruments, such as forceps, can be coated with a particulate therapeutic agent for delivery by applying pressure to the vessel wall with the coated surface of the instrument. Photochemical coupling can be used to secure the therapeutic agent to the vessel walls if the delivery force is not sufficient to deliver the therapeutic agent to a stable location within the vessel wall.

Figure 6:
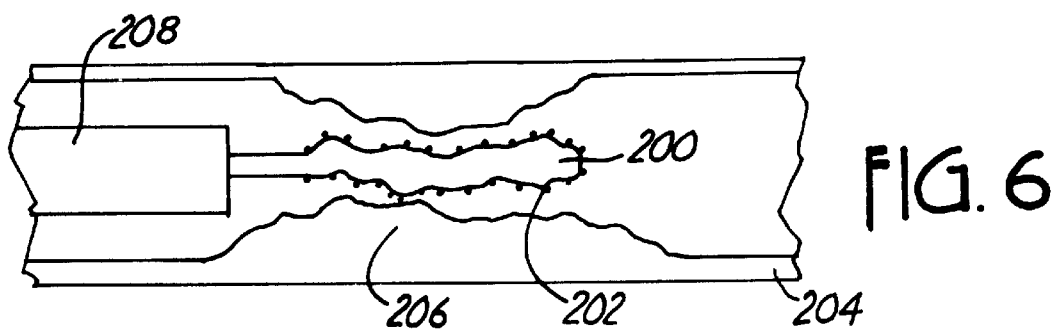
FIG. 6 is a sectional side view of a blood vessel with an angioplasty balloon positioned for use, in which the cross section is taken through the center along the length of the vessel.

Referring to FIG. 6, angioplasty balloon 200 has a deposit of therapeutic particles 202 on its outer surface. Angioplasty balloon 200 is deployed within blood vessel 204 at a point of partial blockage 206. Angioplasty balloon 200 can be deployed through a catheter 208.

Figure 7:
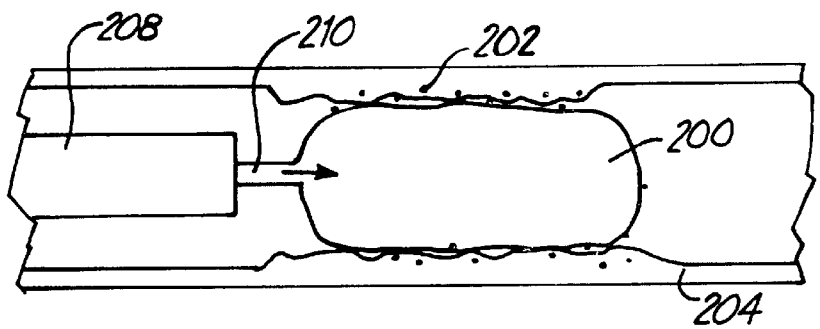
FIG. 7 is a sectional side view of the blood vessel of FIG. 6 with an expanded angioplasty balloon, in which the cross section is taken through the center of the vessel.
Figure 8:
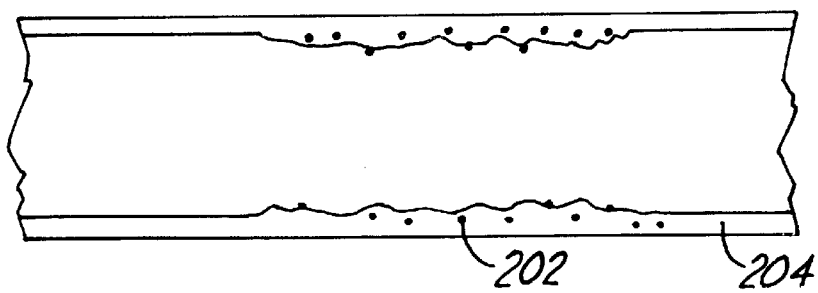
FIG. 8 is a sectional side view of the blood vessel of FIG. 7 wherein the angioplasty balloon and catheter have been removed following deflation of the angioplasty balloon to leave behind therapeutic particles, in which the cross section is taken through the center of the vessel.

Referring to FIG. 7, balloon 200 is expanded by flowing fluid, either a gas or a liquid, into balloon 200 through channel 210. If the fluid is blood compatible, such as sterile saline, balloon 200 can be designed to have the fluid flow through the walls of balloon 200. Balloon 200 generally is deployed for about one minute. When balloon 200 is deployed, at least some of therapeutic particles 202 are deposited within the tissue and/or plaque in the vessel wall. After the balloon is deflated, balloon 200 and catheter 208 are withdrawn from blood vessel following the removal of balloon 200, as shown in FIG. 8.

Biocompatible Materials

The biocompatible medical devices can be made from one or more biocompatible materials described below. Biocompatible materials are suitable for contact with a patient's bodily fluids and tissues. Appropriate biocompatible materials include natural materials, synthetic materials and combinations thereof.

Natural, i.e., biological, material for use in the invention includes relatively intact (cellular) tissue as well as decellularized tissue. These tissues may be obtained from, for example, natural blood vessels, such as veins or arteries, pericardial tissues such as pericardial patches, connective tissues, bypass grafts, blood vessels, dura matter, fascia, submucosa, umbilical tissues, and the like.

Natural tissues are derived from a particular animal species, typically mammalian, such as human, bovine, porcine, canine, seal, kangaroo or transgenic mammals. Suitable natural tissues generally include collagen-containing material. Natural tissue is typically, but not necessarily, soft tissue. Appropriate tissues also include tissue equivalents such as tissue-engineered material involving a cell-repopulated matrix, which can be formed from a polymer of from a decellularized natural tissue. Tissue materials are particularly useful for the formation of vascular grafts.

Tissues can be fixed by crosslinking. This provides mechanical stabilization, for example, by preventing enzymatic degradation of the tissue. Glutaraldehyde is typically used for fixation, but formaldehyde, other difunctional aldehydes, epoxides, genipin or derivatives thereof can be used. Tissues can be used in either crosslinked or uncrosslinked form, depending on the type of tissue, the use and other factors.

Relevant synthetic materials include, for example, polymers, metals and ceramics. Appropriate ceramics include, without limitation, hydroxyapatite, alumina and pyrolytic carbon. Appropriate metals include medals approved for medical use, such as titanium, cobalt, stainless steel, nickel, iron alloys, cobalt alloys. For use in vascular stents, preferred metals include, for example, resilient metals, such as Elgiloy®, a cobalt-chromium-nickel alloy, and MP35N, a nickel-cobalt-titanium alloy. Appropriate synthetic materials include hydrogels and other synthetic materials that cannot withstand severe dehydration.

Polymeric materials can be fabricated from synthetic polymers as well as purified biological polymers. The polymeric materials can be woven into a mesh to form a matrix or substrate. Alternatively, the polymer materials can be molded or cast into appropriate forms. Appropriate synthetic polymers include, without limitation, polyamides (e.g., nylon), polyesters, polystyrenes, polyacrylates, vinyl polymers (e.g., polyethylene, polytetrafluoroethylene, polypropylene and poly vinyl chloride), polycarbonates, polyurethanes, poly dimethyl siloxanes, cellulose acetates, polymethyl methacrylates, ethylene vinyl acetates, polysulfones, nitrocelluloses and similar copolymers.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Other suitable polymers include natural or synthetic resorbable polymers such as dextran, hydroethyl starch, gelatin, derivatives or gelatin, polyvinylpyrrolidone, polyvinylalcohol, poly[N-(2-hydroxylpropyl) methacrylamide], polyglycols, polyesters, poly(orthoesters), poly(ester amides), polyanhydrides. Resorbable polyesters include, for example, poly(hydroxy acids) and copolymers thereof, poly(ε-caprolactone), poly(dimethyl glycolic acid), and poly(hydroxy butyrate). Preferred resorbable polymers include, for example, D,L-polylactic acid, L-polylactic acid, poly(glycolic acid), and copolymers of L-lactic acid, D-lactic acid and glycolic acid.

Biocompatible materials can form the entire medical device or they can form portions of the medical device. Biocompatible materials can include one or a combination of the various natural materials and synthetic materials described above.

Vascular grafts can be primarily tissue based or polymer based. Polyesters, such as polyethylene terephthalates, are particularly suitable for the formation of vascular grafts. To prevent undesirable levels of bleeding through knitted or woven vascular grafts or the like, a small volume of the patient's blood can be forced into and through the graft's interstices prior to implantation. A clot results that is ultimately replaced by ingrowth of fibroblast cells and collagen. Alternatively, the graft can be manufactured with albumin or collagen in the fabric interstices.

Vascular stents can be formed from metals, polymers and combinations thereof. Resorbable polymers are particularly well suited for the formation of temporary vascular stent embodiments. Exogenous storage structures can be attached to the stent with or without a chemical linker based on the binding properties of the material. The binding of a exogenous storage structure to a biocompatible material is described in detail below.

Suitable polymers for the formation of angioplasty balloons include, for example, cellulose acetate, polyvinyl chloride, polysulfone, polyacrylonitrile, polyurethanes, polyolefins, polyesters, fluoropolymers and other natural and synthetic elastomers.

With respect to relevant embodiments, the exogenous storage structures can be associated with an entire biocompatible material or a portion of the biocompatible material. Similarly, if the medical article includes more than one biocompatible material, storage structures can be associated with one or more of the biocompatible materials. For example, an appropriately treated natural blood vessel can be combined with fabric sewing cuffs to form a vascular graft, where the tissue and/or the fabric can be associated with exogenous storage structures.

A medical article can include one or more types of exogenous storage structures and/or one or more therapeutic agents. If a plurality of types of exogenous storage structures are used, the different types of storage structures can be associated with the same biocompatible material(s) or portions thereof, or with different biocompatible material(s) or portions thereof. For example, one type of storage structure can be associated with the tissue portion of a tissue vascular graft while a second type of exogenous storage structure is associated with the sewing cuff. Similarly, a first type of exogenous storage structure can be associated with the entire medical article, such as both the tissue portion and the sewing cuff portion of a vascular graft, while a second type of exogenous storage structure is only associated with the sewing cuff portion. Other variations can be used.

The exogenous storage structures can be associated with the biocompatible material before or after the various components of the medical device are combined into the medical device. The selected approaches for association of the exogenous storage structure with the biocompatible material may influence the order of construction of the medical device.

Therapeutic Agents

The approaches described herein are suitable for the delivery of therapeutic agents to sites susceptible to risk for the development of restenosis. Suitable therapeutic agents are able to inhibit restenosis, for example, by inhibiting platelet deposition, the proliferation of smooth muscle cells and excretion of extracellular matrix or a combination thereof. Exogenous storage structures can be used for the delivery of one or more therapeutic agents in association with a medical device to inhibit the development of restenosis. Preferred therapeutic agents include, for example, ionic agents that can be stored with preferred exogenous storage structures. In alternative embodiments, therapeutic agents are formulated into particulates for delivery from the surface of a medical device. Some therapeutic compounds can be directly covalently bonded to the biocompatible material.

Natural macromolecular storage structures are capable of storing a variety of ionic therapeutic agents. Suitable ionic therapeutic agents include, for example, radioactive ions and ionic nitric oxide (NO) precursors. Nitric oxide is known to inhibit platelet aggregation, as described in U.S. Pat. No. 5,665,077 to Rosen et al., incorporated herein by reference.

Radioactive ions act as antiproliferative agents. Suitable radioactive ions include anions, such as $^{32}PO_4^{-1}$, $^{125}I^-$, $^{131}I^-$, and cations of metals, such as, $^{59}Fe$, $^{67}Ga$, $^{58}Co$, $^{67}Cu$, $^{90}Y$, $^{99}Rh$, $^{186}Re$, and $^{198}Au$. Radioactive ions refer to metal atoms that have been isotopically enhanced relative to any naturally occurring radioactive ions. Radioactive ions of interest generally have half-lives considerably less than a year such that they are not found naturally, although some of the ions can be produced as decay products of long lifetime isotopes, such that very small amounts can occur in nature. Isotopically enhanced radioactive metal atoms/ions are preferably enhanced at least about 10 times relative to any naturally occurring values and more preferably at least 100 times any naturally occurring values. Preferred radioactive isotopes are beta emitters.

Preferred ways of delivering nitric oxide include the delivery of compounds that release nitric oxide. Ionic compounds that decompose to release nitric oxide include, for example, organic and inorganic compounds that include an —NONO⁻ functional group. For example, suitable organic compounds have the structure XNONO⁻, where X can be primary amine, such as $(CH_3)_2CHNH—$, a secondary amine, such as $(CH_3CH_2)_2N—$, or a polyamine, such as, the zwitterionic species with X being spermine, i.e., $H_2N(CH_2)_3NH_2^+(CH_2)_4N[NONO]^-(CH_2)_3NH_2$. A suitable inorganic species is NaO[NONO]Na, nitropercide. The synthesis of 1-(2S-carboxypyrrolidin-1-yl)-1-oxo-2-hydroxydiazene disodium salt, 1-hydroxy-2-oxo-3-carboxymethyl-3-methyl-1-triazene disodium salt, 1-hydroxy-2-oxo-3-carboxymethyl-3-methyl-1-triazine N-methylamide sodium salt, the bis(nitric oxide) adduct of L-prolyl-L-leucylglycinamide, and corresponding protein adducts are described in U.S. Pat. No. 5,632,981 to Saavedra et al., entitled "Biopolymer-Bound Nitric Oxide-Releasing Compositions, Pharmaceutical Compositions Incorporating Same and Methods of Treating Biological Disorders Using Same," incorporated herein by reference. The protein adducts can be used directly as exogenous storage structures in which the nitric oxide-releasing functional groups are the therapeutic agents.

The amine groups of spermine are suitable for covalent bonding to a biocompatible material that has functional groups that bond to the amines. For example, aldehyde functional groups react with amines. Aldehyde crosslinked tissue generally has free aldehyde groups that can bond with the amines. Other nitric oxide releasing compounds can be formulated with reactive functional groups that can be covalently bonded to a biocompatible material with corresponding reactive functional groups.

In certain embodiments, the therapeutic agents are incorporated into a particle that can be delivered from the surface of a medical device into tissue and/or plaque lining the blood vessel wall. The radioactive ions and the ionic nitric oxide releasing compounds described above, along with appropriate counter ions, can be formed into particles or combined with a suitable binder to form particles, as described below. Similarly, exogenous storage structures which are not attached to a medical device can be used as particles for delivery from the surface of a medical device. In addition, non-ionic therapeutic agents can be formed into particles or combined with a suitable binder to form the particles.

Suitable non-ionic therapeutic agents for delivery as particles include, for example, neutral compounds containing the radioactive isotopes listed above and non-ionic nitric oxide-releasing compounds. Suitable non-ionic nitric oxide releasing compounds include, for example, α-substituted nitroso compounds (R—NO, where R is a tertiary carbon group), such as 2-methyl-2-nitrosopropane. These α-substituted nitroso compounds are relatively stable at room temp and decompose at body temperature. Use of α-substituted nitroso compounds as a nitric oxide source is described in U.S. Pat. No. 5,665,077 to Rosen et al., entitled "Nitric Oxide-Releasing Nitroso Compositions and Methods and Intravascular Devices for Using Them to Prevent Restenosis," incorporated herein by reference. Alternatively, insoluble or slightly soluble compounds incorporating radioactive atoms can be formed into powders that are used as the source of particles. For example, ferric phosphate ($FeO_4P$) can incorporate radioactive iron and/or phosphate atoms. Ferric phosphate is practically insoluble in water, and the non-radioactive form of ferric phosphate is used as a food supplement.

Appropriate doses of the agent may depend on several factors, such as size of the blood vessel, physical condition of the patient, nature of the medical device, and the properties of the therapeutic agent. Generally, for nitric oxide-releasing agents, a suitable amount of therapeutic agent releases from about 0.05 mg to about 100 mg of NO. Spermine has an IC-50 concentration, i.e., a concentration at 50 percent effectiveness, of $1.97 \times 10^{-8}$ molar. Thus, an effective amount of spermine would be delivered to yield a local concentration in this order of magnitude or higher. Similarly, an effective concentration of nitro percide is $2.5 \times 10^{-8}$ molar. A suitable treatment period would be about 10 days, such that the cumulative NO quantities would range from about 0.00086 moles to about 0.086 moles. Treatment periods can be extended to longer times, for example, 6 weeks. Over a six week period, the total amounts of NO would be from about 0.0036 moles to about 0.36 moles. Suitable amounts of radioactive compounds will further depend on the isotropic enrichment, the lifetime of the isotope and the penetrative ability of the radiation. For metal ions that are beta emitters with a lifetime over a few days, a suitable amount of radioactive metal ions ranges from about 0.001 milligrams(mg)/gram(g) biocompatible material to about 100 mg/g and preferably from about 0.001 mg/g to about 30 mg/g. The amount of radioactive ions delivered preferably are below toxic levels by a factor of 10 or more, where toxic levels are levels at which observable physical effects of the radiation manifest themselves.

Exogenous Storage Structures

Storage structures can be used for the delivery of cationic or anionic therapeutic agents to a blood vessel. Exogenous storage structures preferably are microscopic, natural macromolecules such as proteins, carbohydrates, nucleic acids and combinations thereof. It is to be understood, however, that aggregations of the preferred compositions need not be microscopic. Suitable macromolecules generally have a molecular weight greater than about 5,000 atomic mass units (amu), preferably greater than about 10,000 amu and more preferably greater than about 25,000 amu. The term "protein" includes peptides and polypeptides alone as well as peptides and polypeptides conjugated with carbohydrates, nucleic acids, lipids and/or other compounds.

Exogenous storage structures are distinct from any naturally occurring structures, such as ferritin already present in the material. In other words, exogenous storage structures are non-inherent or extrinsic structures that are associated with the biocompatible material, as depicted in FIG. 1. Exogenous structures are in contrast with endogenous structures that are inherent to the biocompatible materials. Generally, the exogenous storage structures are attached as discrete entities to the biocompatible material, using the methods described below, rather than applied as a coating.

Appropriate protein storage structures within the scope of the present invention include metal binding proteins such as ferritin, transferrin, hemoglobin, globulins, albumin, glutathione, metallothiens, myoglobin, ceruloplasmin and hemacyanin, as well as modified proteins having attached bifunctional chelators to generate metal binding capability. Ferritin is a preferred metal binding protein because of its generally large storage capacity.

Ferritin protein without bound metal is called apoferritin. Apoferritin is a 24-subunit protein with a molecular weight of approximately 45,000 amu, although the molecular weight varies depending on the animal species from which the ferritin is isolated. Isoferritins, related proteins with differing numbers of subunits, are also within the scope of the present invention and are included within the term "ferritin."

The ferritin core can store between about 2000 and about 4500 iron ions. For example, horse spleen ferritin can bind about 4500 iron ions, while human ferritin can bind about 2500 iron ions. The iron is stored within the core as ferric oxide or ferric hydroxyphosphate. Ferritin can also bind large quantities of other metal cations, as well as anions that are bound to generally maintain, overall electrical neutrality. Binding of these non-iron ions is enhanced by the simultaneous binding of a moderate quantity of iron ions. Generally, storage structures, such as ferritin, can be bound to biocompatible material with the storage structures preloaded in vitro with desired cations or anions.

The selection of a particular storage structure can be based on its storage capacity, availability and ease of handling. For example, ferritin or other metal binding proteins generally need not be saturated with the metal ions or ions of interest to be useful in the invention. The ferritin can be charged with, for example, desired ions by incubating purified ferritin with a relatively concentrated solution of the ions. The binding of the ions to the protein can be accelerated by heating and by pH adjustment. After a sufficient period of incubation, the free ions can be removed by passing the solution over an ion exchange resin or through a size exclusion membrane.

In addition, storage structures can be formed from other proteins modified to create metal binding capability. Preferred proteins for modification have high molecular weight, such as immunoglobulins. The modification can involve, for example, covalent bonding of metal sequestering compounds to the protein.

More specifically, significant metal binding capability can be created by binding a bifunctional chelator, such as a polyaminocarboxylate or a polyaminophosphonate, to the protein as the metal sequestering compound. Preferred bifunctional chelators include electrohilic and nucleophilic moieties such as bromoacetamide, maleimide, imidoester, thiophthalimide, N-hydroxysuccinimyl ester, pyridyl disulfide, phenyl azide, o-acylisourea, diazonium hydrazine, carbonyl hydrazine, amino hydrazine, acyl hydrazine, diazonium semicarbazide, carbonyl semicarbazide, amino semicarbazide, acyl semicarbazide, thio semicarbazides and cyclic polyaminocarboxylates and cyclic polyaminophosphonates having 12 to 16 atom rings. The specific chelator can be selected to produce a desired release rate of the bound ions if release is a consideration for function.

The bifunctional chelators generally can be covalently bonded to the protein by conventional methods. Typically, the covalent bonds will be formed between selected amino acid residues of the protein and a specific functional group in the chelator, in which the distinct functional groups are distinct from the metal chelating sites. The number of chelating agents bound to a protein will depend on the structures of the chelator and protein and on the reaction conditions.

It is preferable to have at least one bifunctional chelator bound to each protein, and it is more preferable to have multiple bifunctional chelators bound to each protein. Metal ions can be bound to the chelator before, at the time of, or after the covalent binding of the chelator to the protein. The reaction conditions may influence the selected order of the processing steps.

In addition, organic anions R-NONO$^-$ with NONO$^-$ functional groups can be attached directly onto protein side chains or other natural macromolecules by way of other reactive functional groups located in the R group. In this way a variety of natural macromolecules can be modified to delivery NO as a therapeutic agent.

Binding of Exogenous Storage Structures to Biocompatible Material

Binding of the exogenous storage structures to the biocompatible material can involve specific binding interactions to target specific structures within the material. Alternatively, the binding can involve covalent bonding due, for example, to reaction with general crosslinking agents or other specifically designed linker molecules. For tissue substrates, the binding of the exogenous storage structures preferably takes place at or near a physiological pH, preferably ranging from a pH of about 6 to a pH of about 8.5 and more preferably from a pH of about 7.0 to a pH of about 8.0.

One procedure for non-specific binding makes use of glutaraldehyde, which crosslinks proteins by way of two aldehyde groups. This procedure is particularly appropriate for binding protein exogenous storage structures to tissue based biocompatible material. Since glutaraldehyde is typically used for fixation of some biocompatible material, e.g. tissues, the non-specific crosslinking to bind the exogenous storage structures to the tissue material can be performed simultaneously with fixation of the tissue. Alternatively, the non-specific binding of the exogenous storage structures to the biocompatible material can be performed as a separate step before or after the completion of a fixation process, assuming a fixation step is performed.

Similarly, the exogenous storage structure can be bound directly or indirectly to the biocompatible material using other covalent chemical bonding reactions. For example, other polyfunctional linker molecules, besides dialdehydes, can be used to join the exogenous storage structure and the biocompatible material. At least one functional group of the polyfunctional linker molecule reacts with the exogenous storage structure, and at least one functional group of the polyfunctional linker molecule reacts with the biocompatible material. For example, with a synthetic polymer biocompatible material, the linker molecule can react with a functional group in the polymer. In particular, if the polymer is polyester, such as polyethylene terephthalates, ester functional groups can decompose or contain residual carboxyl groups. For polyesters, the linker can include a carbodiimide, such as in the compound 1-ethyl-3[3-dimethylaminopropyl]-carbodiimide hydrochloride (EDC), functional group to bond with the polymer and an aldehyde functional group to bond with, for example, a protein storage structure. Use of a photoactivated linker is described below.

If the storage structure includes appropriate functional groups to bond with the biocompatible material directly, a linker molecule may not be necessary.

Specific binding interactions can form a basis for attachment of the exogenous storage structures. The character of the specific binding interactions involve a plurality of non-covalent interactions such as hydrogen bonding, van der Waals interactions and molecular rearrangements, which characterize, for example, antibody-antigen, specific binding protein-receptor and enzyme-substrate associations. Thus, specific binding interactions involve molecular recognition characteristics wherein a plurality of interactions over a region of both interacting molecules are involved to bind or dock the two molecules together.

One approach for taking advantage of specific binding interactions involves covalent binding of a linker to the storage structure and association of the linker with the prosthetic material by specific binding interactions. A variety of commercially available antibodies, receptors, substrates and other specific binding reagents may be used as linkers. Such linkers can function as binding molecules for cellular or extracellular sites in tissue having specific binding sites. Similar binding can be used for synthetic materials if, for example, antibodies were raised against the synthetic materials.

As an alternative to using commercially available antibodies, cellular or extracellular components from the biological material can be isolated by conventional techniques. For example, nuclear membranes or a specific portion of the nuclear membrane corresponding to an antigen or groupings of antigens can be isolated. The isolated materials then are used to produce polyclonal or monoclonal antibodies by conventional techniques. The resulting antibodies are covalently bonded to the exogenous storage structure to prepare it for binding to the biocompatible material.

A storage structure having an attached antibody or nay other comparable targeting molecule is considered a "storage structure" for the purposes of the present application. The binding of compounds to antibodies is well established, especially where the compound is a protein. Due to its high iron content, ferritin is commonly linked to antibodies to serve as an electron microscopy probe in the histology field. In a preferred embodiment, glutaraldehyde is used to join the respective proteins. In addition, as noted above, the antibody itself can be modified with a therapeutic agent to become, itself, an exogenous storage structure, rather than serving as a linker portion of an exogenous storage structure.

In an alternative embodiment, photochemical coupling can be used for covalent coupling. Photochemical coupling is based on the use of high energy light, e.g., ultraviolet light, to form reactive intermediates of certain functional groups. These reactive intermediates can form carbon-carbon bonds between two compositions. Aryl ketone functional groups are particularly useful in this respect.

Photochemical coupling is particularly appropriate for the attachment of exogenous storage structures to synthetic polymeric materials, uncrosslinked tissues or biological polymers. See, for example, Dunkirk et al., J. Biomaterials Applications 6:131–156 (1991), incorporated herein by reference. Photochemical techniques are useful also for the attachment of exogenous storage structures to metal surfaces and decellularized tissue substrates. Photochemical coupling can be used for the direct attachment of an exogenous storage structure to the biocompatible material. Alternatively, photochemical coupling can be used to attach a linker to the biocompatible material either before or after the attachment of the linker to the exogenous storage structure.

In addition, photochemical coupling can be used to attach a therapeutic agent directly to tissue or plaque following delivery as particles into the vessel wall or other region susceptible to restenosis. Light is directed into the vessel following delivery of the therapeutic agent.

A specific embodiment of photochemical coupling involves the use of a linker with a functional group that reacts with primary amines and a second functional group that reacts with functional groups of the biocompatible material only following activation by ultraviolet light. Thus, if the exogenous storage structure has primary amine functional groups, the linker can attach to the exogenous storage structure. The linker with bound exogenous storage structure is contacted with the biocompatible material. Then, ultraviolet light is used to activate the second functional group of the linker and bind the exogenous storage structure to the biocompatible material.

A suitable difunctional compound is N-5-azido-2-nitrobenzoyloxysuccinimide (ANB-NOS). The ANB-NOS compound reacts with primary amines of the exogenous storage structure, such as ferritin, as shown in the following reaction:

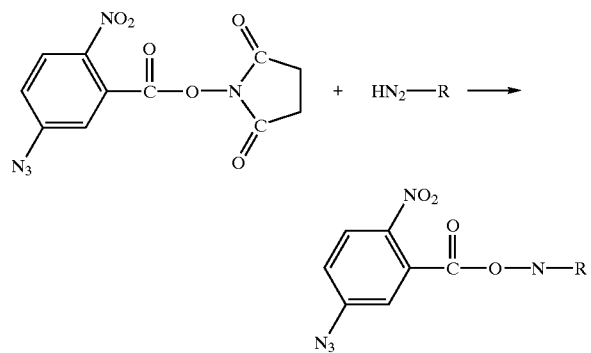

where R is the ferritin protein or other amine containing exogenous storage structure. Upon exposure to ultraviolet light, a ring expansion takes place to form a highly reactive species, as indicated in the following:

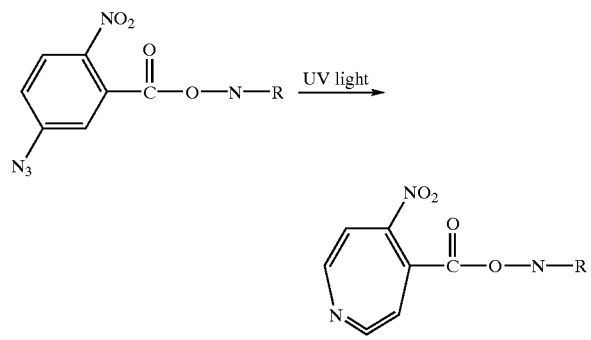

The ring expanded compound is highly reactive and will react with crosslinked tissue or other biocompatible materials, as shown below for reaction with an amine:

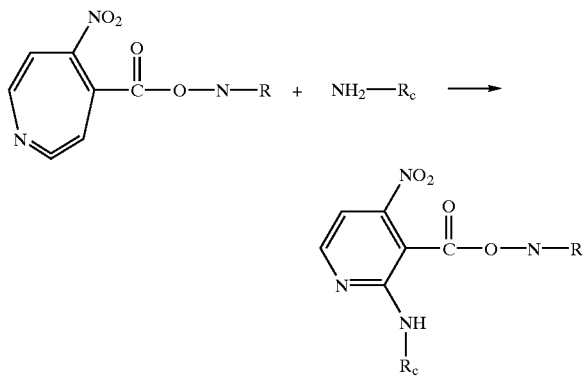

where $R_c$ is the tissue or other biocompatible material.

ANB-NOS can also be used with therapeutic agents delivered directly into or onto the walls of a blood vessel. The ANB-NOS compound is reacted with amine groups of the therapeutic agent. The complex formed as the reaction product of ANB-NOS with the therapeutic agent is delivered into the walls of the blood vessel or other region susceptible to restenosis. Then, ultraviolet light is directed at the blood vessel with the complex. Absorption of the ultraviolet light results in the ring expansion and subsequent reaction with the tissue or plaque by the highly reactive ring expanded compound. In this way, the therapeutic agent is bound to the vessel walls.

Covalent Bonding of Therapeutic Agent

As noted above the therapeutic agent can be directly covalently bonded to the biocompatible material. This approach is similar to the use of an exogenous storage structure except that no macromolecular structure is used to store the therapeutic agent. However, there is generally at least a portion of the compound, e.g., spermine, that acts to support the active therapeutic portion of the compound, such as a radioactive atom or NONO group. The entire portion of the exogenous compound bound to the biocompatible material can be considered the therapeutic agent.

As noted above, spermine can be used to link a nitric oxide releasing group NONO to a biocompatible material using amine groups. Similar organic and inorganic compounds with NONO groups and other reactive functional groups can be bonded to a biocompatible material to introduce nitric oxide releasing activity. In addition, metal chelators can be produced with reactive functional groups. Rather than reacting the functional groups with a macromolecule to form an exogenous storage structure, the metal chelators can be covalently bonded directly with the biocompatible material. Radioactive metal ions can be associated with the chelator prior to or after bonding the chelator to the biocompatible material.

Particulate Agents

In some embodiments, the therapeutic agent is formulated into a particle for delivery to a blood vessel wall or other region susceptible to restenosis. The particle is applied to the outer surface of an expandable medical device of an otherwise flexible or movable medical device for delivery. The particles should remain in a particulate form on the outer surface of the medical device since delivery of identifiable particles will occur more readily than other coatings. When the medical device is expanded to contact the targeted region, the force of the expansion propels the particulates into the tissue and/or plaque of the contacted walls. The particles can be formed directly from the therapeutic agent or the therapeutic agent can be formed into particles using a binder or the like. The binder can be an exogenous storage structure or a matrix into which the therapeutic agent is incorporated.

The discrete nature of the particles, even with some aggregation typical of particles in a powder, results in some penetration of the particles into the walls contacted by the delivery device. Thus, especially in the case of an angioplasty balloon, the blood flow does not easily remove the therapeutic agent after it is deposited. When an angioplasty balloon is used to deposit the therapeutic agent, at least a portion of the particles of therapeutic agent remain after the angioplasty balloon is removed.

Suitable particles include the exogenous storage structures described above. To function as particulates, the storage structures are deposited without any binding to the biocompatible material. Since there is no binding with the biocompatible material, the storage structures can be applied to the biocompatible material and, subsequently, deposited into the blood vessel wall or other region susceptible to restenosis.

Alternatively, the particles can be formed by incorporating the therapeutic agents into a polymer matrices. Suitable polymers include synthetic polymers and purified natural polymers, such as those described above. The polymers with the therapeutic agent can be formed into particles of appropriate size to apply onto the biocompatible material and for deposition into the targeted region. The therapeutic agent can be incorporated into the polymer matrix using an appropriate technique based on the nature of the therapeutic agent and the polymer. For example, a polymer particle can be formed by spray drying a polymer solution from a non-aqueous solvent where the solution contains a dissolved composition with radioactive atoms. Preferably, the radioactive composition is sparingly soluble in aqueous solutions. For therapeutic agents that are sufficiently heat insensitive, the particles can be formed from a polymer melt.

Furthermore, some therapeutic agents themselves can be formed into particles. In particular, inorganic compounds that are relatively insoluble in aqueous solutions, such as radioactive ferric phosphate, can be formed into fine powders comprised of suitable particles for delivery under the approaches described herein. These inorganic compounds can include appropriate radioactive atoms.

The particles can be deposited on the surface of the medical device using a dispersion of the particles. The dispersion can be applied as a spray, by dipping the medical device into the dispersion or any other reasonable application approach. The liquid used to deposit the particles can be removed by drying the particles and do not need to remain moist. Following application of the particles, the medical device can be stored appropriately to maintain the particles appropriately on the surface of the medical device.

Combination of Treatments

A plurality of therapeutic agents and/or delivery approaches can be used in association with a single medical device. With respect to combinations of therapeutic agents, a plurality of radioactive isotopes can be delivered, where the different isotopes have different lifetimes and/or emit radiation with different penetration distances. Similarly, radioactive isotopes can be used along with a nitric oxide-releasing agent, such that both radiation and nitric oxide can be delivered to inhibit restenosis.

Combinations of therapeutic agents can be delivered in similar ways or with different delivery approaches. For example, a plurality of therapeutic agents can be combined within a single portion of exogenous storage structures. In this way, association of this single portion exogenous storage structure with a biocompatible material would deliver the plurality of therapeutic agents. Similarly, different therapeutic agents can be associated each with different portion of exogenous storage structures. Each portion of exogenous storage structures can be equivalent to other portions of exogenous storage structures or of different type from other portions of exogenous storage structures used with different therapeutic agents.

For example, a nitric oxide releasing compound can be bound to a hemoglobin protein as an exogenous storage structure, while radioactive metal cations are associated with ferritin protein as an exogenous storage structure. After the proteins are loaded with therapeutic agent, the storage structures can be bound to a biocompatible material simultaneously or sequentially. In addition, one or more therapeutic agents can be directly bonded to the biocompatible material.

Similarly, for embodiments based on application of particles on the surface of a medical device, individual particles can incorporate a plurality of therapeutic agents, or different therapeutic agents can be segregated within different quantities of particles that are then applied to the surface of the medical device simultaneously or sequentially. Different therapeutic agents can be applied to the same portion of a biocompatible material or to different portions of a biocompatible material.

In this application, approaches have been described for the delivery of therapeutic agents with bound exogenous storage structures as well as with particles that are applied on the surface of an expandable medical device. These approaches can be combined using the same therapeutic agent or with different therapeutic agents. For example, a particular therapeutic agent can be bound in an exogenous storage structure that is bound to a medical device and applied as particles. Alternatively, a therapeutic agent can be bound in an exogenous storage structure and within a different matrix to form particles. The exogenous storage structures are bound to the medical device while the particles are applied to the surface of the medical device. Similarly, a plurality of therapeutic agents can be applied in various combinations and forms.

When both bound exogenous storage structures and surface applied particles are used on an expandable medical device, deployment of the device deposits the particles within the vessel wall or other region susceptible to restinosis and leaves the exogenous storage structures in association with the medical device. This combination approach can be particularly advantageous with vascular stents. The exogenous storage structures can be bound to all or a portion of the stent, while the therapeutic particles are bound to the outside of the stent. When the stent is deployed, such that is expands to support the blood vessel wall, at least some of the particles on the outside of the stent are deposited in the vessel wall and the exogenous storage structures remain associated with the stent. The therapeutic agents associated with the particles and with the exogenous storage structures can both be effective to inhibit restenosis. Direct bonding of the therapeutic agent can be used in place of the exogenous storage structures.

Storage, Packaging, Distribution and Use

If the assembly process is not harsh, the medical device can be assembled following the association of therapeutic agent with the biocompatible material. Alternatively, the therapeutic agent can be associated with the biocompatible material following the assembly of the medical device. If the medical device includes multiple biocompatible materials that are assembled into the medical device, the therapeutic agents can be associated with one or more of the biocompatible materials. For example, a vascular graft can include a therapeutic agent associated with the walls of the graft and/or associated with a sewing cuff or the like.

The biocompatible material with associated therapeutic agent can be stored appropriately prior to and following formation into a medical device. Appropriate storage conditions will depend significantly on the nature of the biocompatible material and the therapeutic agent/storage structure. For example, tissue biocompatible materials generally should be kept moist to prevent irreversible degradation of the material. The tissue can be immersed in a liquid such as an aqueous glutaraldehyde solution to keep the tissue moist. Even if the biocompatible material is not moisture requiring, some storage structures, such as biological macromolecules, may require moisture to avoid degrading. Materials with moisture requiring storage structures can be stored by immersing the material or by storage in a moist atmosphere.

Immersion of a biocompatible material is appropriate with therapeutic agents stored in exogenous storage structures or with therapeutic agents covalently bonded to the biocompatible material, but may not be appropriate with particles deposited on the exterior of the medical article. However, moisture sensitive composites of biocompatible material and therapeutic agents can be stored in a moist environment, for example, using a storage container that generates a moist environment without immersing the device. Such a storage container is described in U.S. Pat. No. 5,960,956 to Langanki et al., entitled "Storage Container," incorporated herein by reference. If neither the biocompatible material nor the therapeutic agent including any exogenous storage structures are moisture requiring, the biocompatible material with the therapeutic agent can be stored in a dry, sterile environment.

For distribution, the medical devices are placed in sealed and sterile containers. The containers can be dated such that the date reflects the maximum advisable storage time, if components of the medical device should not be stored indefinitely. The containers are packaged along with instructions for the proper use and/or implantation of the medical device and along with other appropriate and/or required labeling. The containers are distributed to health care professionals for use in appropriate medical procedures, such as implantation of a prosthesis, temporary deployment of an angioplasty balloon and the like.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. A medical device suitable for implantation comprising a biocompatible material and a plurality of exogenous biological macromolecules bound to the biocompatible material, the exogenous biological macromolecules storing a therapeutic agent that acts to inhibit restenosis, wherein the device comprises a vascular graft and wherein the therapeutic agent comprises radioactive isotopes, the exogenous biological macromolecules being selected from the group consisting of carbohydrates, nucleic acids, natural metal binding proteins and combinations thereof.

2. The medical device of claim 1 wherein the biocompatible material comprises tissue.

3. The medical device of claim 2 wherein the tissue is crosslinked.

4. The medical device of claim 1 wherein the biocompatible material comprises a synthetic polymer.

5. The medical device of claim 1 wherein the exogenous biological macromolecule comprises a molecule selected from the group consisting of ferritin, transferrin, hemoglobin, metal binding globulins, albumin, glutathione, metallothiens, myoglobin, ceruloplasmin and hemocyanin.

6. The medical device of claim 1 wherein the exogenous biological macromolecule compromises a protein.

7. The medical device of claim 1 wherein the exogenous biological macromolecule comprises a ferritin.

8. The medical device of claim 1 wherein the binding of the exogenous biological macromolecules with the biocompatible material involves covalent bonds or specific binding interactions.

9. The medical device of claim 1 wherein the binding of the exogenous biological macromolecules with the biocompatible material involves covalent bonding with a chemical crosslinking agent.

10. The medical device of claim 1 wherein the therapeutic agent comprises metal ions.

11. The medical device of claim 1 wherein the therapeutic agent comprises radioactive metal ions.

12. The medical device of claim 1 wherein the therapeutic agent comprises a nitric oxide source.

13. A medical device suitable for implantation comprising a biocompatible material and a therapeutic agent bound to the biocompatible material, wherein the binding of the therapeutic agent with the biocompatible material involves specific binding interactions, wherein the therapeutic agent comprises an exogenous macromolecular storage structure that is not directly involved in the specific binding interaction.

14. The medical device of claim 13 wherein the exogenous storage structures comprise a synthetic polymer.

15. The medical device of claim 13 wherein the exogenous storage structure comprises a biological macromolecule.

16. A medical device suitable for implantation comprising a biocompatible material and a therapeutic agent covalently bonded to the biocompatible material, the therapeutic agent acting to inhibit restenosis, wherein the therapeutic agent comprises exogenous biological macromolecules selected from the group consisting of carbohydrates, nucleic acids, natural metal binding proteins and combinations thereof.

17. The medical device of claim 16 wherein the therapeutic agent comprises isotopically enhanced radioactive metal ions.

18. The medical device of claim 16 wherein the therapeutic agent releases nitric oxide.

19. A medical device comprising an expandable structure and therapeutic particle on the surface of the expandable structure, the therapeutic particles comprising a therapeutic agent that acts to inhibit restenosis, wherein the therapeutic particles are selected from the group consisting of therapeutic composition within biological macromolecule exogenous storage structures and inorganic particles, and wherein the biological macromolecular exogenous storage structures are selected from the group consisting of carbohydrates, nucleic acids, natural metal binding proteins and combinations thereof.

20. The medical device of claim 19 wherein the expandable structure comprises an angioplasty balloon.

21. The medical device of claim 19 wherein the expandable structure comprises an expandable frame of a vascular stent.

22. The medical device of claim 19 wherein the therapeutic particles comprise inorganic powders.

23. The medical device of claim 19 wherein the therapeutic particles comprise biological macromolecules.

24. The medical device of claim 19 wherein the therapeutic particles comprise a polymer.

25. The medical device of claim 19 wherein the therapeutic agent comprises radioactive atoms.

26. The medical device of claim 19 wherein the therapeutic agent comprises a nitric oxide-releasing compound.

27. A medical device comprising an expandable structure and therapeutic particle on the surface of the expandable structure, the therapeutic particles comprising a therapeutic agent that acts to inhibit restenosis, wherein the therapeutic particles comprise a therapeutic agent within a polymer matrix wherein the medical device is selected from the group consisting of vascular stents, prosthetic conduits, valved grafts, urinary stents, structural stents, vascular shunts, intrauterin devices, in-dwelling percutaneous devices and coronary stents.

28. The medical article of claim 27 wherein the therapeutic agent is selected from the group consisting of metal ions, radioactive atoms and a nitric oxide source.

29. A medical device suitable for implantation comprising a biocompatible material and a plurality of metal binding proteins covalently bonded to the biocompatible material, the metal binding proteins storing a therapeutic agent that acts to inhibit restenosis.

30. The medical device of claim 29 wherein the device comprises a vascular graft.

31. The medical device of claim 29 wherein the therapeutic agent comprises isotopically enhanced radioactive isotopes.

* * * * *